United States Patent
Sun et al.

(10) Patent No.: US 7,053,216 B2
(45) Date of Patent: May 30, 2006

(54) MODULATORS OF RHO C ACTIVITY

(75) Inventors: Dongxu Sun, Mountain View, CA (US); Edward L. Perkins, Duluth, MN (US); Stuart Tugendreich, Mountain View, CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 516 days.

(21) Appl. No.: 10/300,651

(22) Filed: Nov. 19, 2002

(65) Prior Publication Data

US 2003/0171387 A1    Sep. 11, 2003

Related U.S. Application Data

(60) Provisional application No. 60/331,755, filed on Nov. 19, 2001.

(51) Int. Cl.
C07D 239/72    (2006.01)
A61K 31/517    (2006.01)

(52) U.S. Cl. ............... 544/287; 514/266.3; 514/266.31; 514/266.4

(58) Field of Classification Search ............. 514/266.3, 514/266.31, 266.4; 544/287
See application file for complete search history.

(56) References Cited

U.S. PATENT DOCUMENTS

| | | | | | |
|---|---|---|---|---|---|
| 2,651,632 | A | * | 9/1953 | Baker et al. | 544/287 |
| 3,047,462 | A | * | 7/1962 | George et al. | 514/266.3 |
| 3,060,090 | A | * | 10/1962 | Becker | 514/266.31 |
| 3,135,659 | A | * | 6/1964 | Bola et al. | 514/266.31 |
| 3,304,304 | A | * | 2/1967 | Henricus et al. | 544/287 |
| 3,317,388 | A | * | 5/1967 | Bola et al. | 514/266.31 |
| 3,515,787 | A | * | 6/1970 | Brener et al. | 514/266.31 |
| 3,558,610 | A | * | 1/1971 | Brener et al. | 544/287 |
| 3,651,230 | A | * | 3/1972 | Yamamoto et al. | 514/266.31 |
| 3,696,102 | A | * | 10/1972 | Cronin | 544/287 |
| 3,714,354 | A | * | 1/1973 | Stam | 514/266.3 |
| 3,755,581 | A | * | 8/1973 | Janiak | 514/266.31 |
| 3,907,995 | A | * | 9/1975 | Yabutani et al. | 514/266.31 |
| 3,991,193 | A | * | 11/1976 | Taylor et al. | 514/266.31 |
| 4,054,658 | A | * | 10/1977 | Buehler et al. | 514/266.31 |
| 4,668,682 | A | * | 5/1987 | Sekiya et al. | 514/266.2 |
| 4,714,702 | A | * | 12/1987 | Inoue et al. | 514/266.31 |
| 5,283,247 | A | * | 2/1994 | Dwivedi et al. | 514/266.21 |
| 5,470,878 | A | | 11/1995 | Michnick et al. | 514/558 |
| 5,948,775 | A | * | 9/1999 | Koko et al. | 514/217.06 |
| 6,136,812 | A | * | 10/2000 | Chenard et al. | 514/266.2 |
| 6,303,615 | B1 | * | 10/2001 | Elliott et al. | 514/266.2 |
| 6,331,555 | B1 | * | 12/2001 | Hirth et al. | 514/378 |
| 6,545,004 | B1 | * | 4/2003 | Finer et al. | 514/266.2 |

FOREIGN PATENT DOCUMENTS

| | | |
|---|---|---|
| JP | 10-259176 A2 | 9/1998 |
| WO | WO 96/28430 A1 | 9/1996 |
| WO | WO 97/43276 A1 | 11/1997 |
| WO | WO 99/24563 A1 | 5/1999 |
| WO | WO 01/030768 A1 | 5/2001 |

OTHER PUBLICATIONS

Debnath, K. A. et. al., "Structure-Based Identification of Small Molecule Antiviral Compounds . . . ", J. Med. Chem., 1999, vol. 42, No. 17, pp. 3203-3209.*
Badr, M.Z.A. et.al., "Electronic impact-promoted fragmentation of some substituted 4-quinazolones." Chem. Abs., 1997, vol. 124, Abstract #175,225.*
Parasharya, P.M. et. al., "4-(3-H)-Quinazolones: . . . " Chem. Abs., 1997, vol. 121, Abstract #134,062.*
Aktories, "Rho proteins: targets for bacterial toxins," *Trends Microbiol.* 5(7):282-288, 1997.
Boman et al., "Arf proteins: the membrane traffic police?" *Trends Biochem. Sci.* 20(4):147-150, 1995.
Box, "ras Oncogenes in human cancer: a review," *Cancer Res.* 49(17):4682-4689, 1989.
Cerione et al., "The Dbl family of oncogenes," *Curr. Ipin. Cell Biol.* 8(2):216-222, 1996.

(Continued)

Primary Examiner—James O. Wilson
Assistant Examiner—Tamthom N. Truong
(74) Attorney, Agent, or Firm—Howrey LLP; Adam K. Whiting

(57) ABSTRACT

Compounds of formula 1 modulate the activity of Rho C:

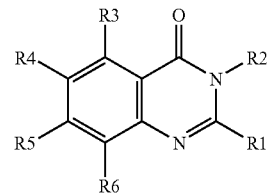

wherein $R_1$ is H, lower alkyl, aralkyl, aryl-lower alkenyl, or —$(CH_2)_n CH(R_7)NR_8 R_9$, where n is 0–6 inclusive, $R_7$ is H, lower alkyl, aryl, or aralkyl, $R_8$ is H, lower alkyl, cyclo-alkyl, aryl, or aralkyl, and $R_9$ is R, RCO—, ROCO—, or RNHCO—, where R is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy;
$R_2$ is lower alkyl, aryl, aralkyl, or —$(CHR_{10})_m$—(CO)—$R_{11}$, wherein m is 0–4, $R_{10}$ is H or lower alkyl, and $R_{11}$ is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy;
$R_3$, $R_4$, $R_5$, and $R_6$, are each independently H, lower alkyl, halo, nitro, OH, lower alkoxy, $NH_2$, lower alkylamino, di(lower alkylamino), trifluoromethyl, or SH;
or a pharmaceutically acceptable salt thereof.

4 Claims, No Drawings

OTHER PUBLICATIONS

Chavrier et al., "The role of ARF and Rab GTPases in membrane transport," *Curr. Opin. Cell Biol.* 11(4):466-475, 1999.

Clark et al., "Genomic analysis of metastasis reveals an essential role for RhoC," *Nature* 406:532-535, 2000.

End, "Farnesyl protein transferase inhibitors and other therapies targeting the Ras signal transduction pathway," *Invest New Drugs* 17(3):241-258, 1999.

Fritz et al., "Rho GTPases are over-expressed in human tumors," *Int. J. Cancer* 81(5):682-687, 1999.

Ganguly et al., "Detection and structural characterization of Ras oncoprotein-inhibitors complexes by electrospray mass spectrometry," *Bioorg. Med. Chem.* 5(5):817-820, 1997.

Ganguly et al., "Interaction of a novel GDP exchange inhibitor with the Ras protein," *Biochemistry* 37(45):15631-15637, 1998.

Hall, "Ras-related proteins," *Curr.Opin. Cell Biol.* 5(2):265-268, 1993.

Hall, "Rho GTPases and the actin cytoskeleton," *Science* 279:509-514, 1998.

Helliwell et al., "The Rho1 effector Pkc1, but not Bni1, mediates signalling from Tor2 to the actin cytoskeleton," *Curr. Biol.* 8(22):1211-1214, 1998.

Ihara et al., "Crystal structure of human RhoA in a dominantly active form complexed with a GTP analogue," *J. Biol. Chem.* 273(16):9656-9666, 1998.

Kaibuchi et al., "Regulation of the cytoskeleton and cell adhesion by the Rho family GTPases in mammalian cells," *Ann. Rev. Biochem.* 68:459-486, 1999.

Kohl, "Farnesyltransferase inhibitors preclinical development," *Ann. NY Acad. Sci.* 886:91-102, 1999.

Kumar et al., "SCH 51344, an inhibitor of Ras/Rac-mediated cell morphology pathway," *Ann. NY Acad. Sci* 886:122-131, 1999.

Longenecker et al., "How RhoGDI binds Rho," *Acta Crystallogr. D. Biol. Crystallogr* 55(Pt 9):1503-1515, 1999.

Mackay et al., "Rho GTPases," *J. Biol. Chem.* 273:20685-20688, 1998.

Maesaki et al., "The structural basis of Rho effector recognition revealed by the crystal structure of human RhoA complexed with the effector domain of PKN/PRK1," *Mol. Cell* 4(5):793-803, 1999.

Maesaki et al., "Biochemical and crystallographic characterization of a Rho effector domain of the protein serine/threonine kinase N in a complex with RhoA," *J. Struct. Biol.* 126:166-170, 1999.

Martinez et al., "Rab proteins," *Biochem Biophys Acta* 1404(1-2):101-112, 1998.

Moore, "Ran and nuclear transport," *J. Biol. Chem.* 273(36):22857-22860, 1998.

Nomanbhoy et al., "Kinetics of cdc42 membrane extraction by Rho-GDI monitored by real-time fluorescence resonance energy transfer," *Biochemistry* 38(6):1744-1750, 1999.

Read et al., "Human RhoA/RhoGDI complex expressed in yeast: GTP exchange is sufficient for translocation of RhoA to liposomes," *Protein Sci.* 9(2):376-386, 2000.

Rittinger et al., "Crystal structure of a small G protein in complex with the GTPase-activating protein rhoGAP," *Nature* 388:693-697, 1997.

Rush et al., "The small nuclear GTPase ran: how much does it run?" *Bioessays* 18(2):103-112, 1996.

Schmidt et al., "Bacterial cytotoxins target Rho GTPases," *Naturwissenschaften* 85(6):253-261, 1998.

Schimmöller et al., "Rab GTPases, directors of vesicle docking," *J. Biol. Chem.* 273(35):22161-22214, 1998.

Shimizu et al., "An open conformation of switch I revealed by the crystal structure of a $Mg^{2+}$-free form of RHOA complexed with GDP,"*J. Biol. Chem.* 275(24):18311-18317, 2000.

Suwa et al., "Overexpression of the rhoC gene correlates with progression of ductal adenocarcinoma of the pancreas," *Br. J. Cancer* 77(1): 147-152, 1998.

Tanaka et al., "Control of reorganization of the actin cytoskeleton by Rho family small GTP-binding proteins in yeast," *Curr. Opin. Cell Biol.* 10(1):112-116, 1998.

Taveras et al., "Ras oncoprotein inhibitors: the discovery of potent, Ras nucleotide exchange inhibitors and the structural determination of a drug-protein complex," *Bioorg. Med. Chem.* 5(1):125-133, 1997.

Vojtek et al., "Increasing complexity of the Ras signaling pathway," *J. Biol. Chem.* 273(32):19925-19928, 1998.

Watanabe et al., "Cooperation between mDia1 and ROCK in Rho-induced actin reorganization,"*Nat. Cell Biol.* 1(3):136-143, 1999.

Whitehead et al., "Dbl family proteins," *Biochem. Biophys. Acta* 1332(1):F1-23, 1997.

Yoshioka et al., "Overexpression of small GTP-binding protein RhoA promotes invasion of tumor cells," *Cancer Res.* 59(8):2004-2010, 1999.

Gershbein et al., "Action of drugs and chemical agents on rat liver regeneration," *Chem. Abst.* 103(21): Abstract #103:172042b, 1985.

* cited by examiner

MODULATORS OF RHO C ACTIVITY

CROSS-REFERENCE TO RELATED APPLICATIONS

This application claims the benefit of provisional patent application Ser. No. 60/331,755 filed Nov. 19, 2001, from which application priority is claimed under 35 USC § 119(e)(1) and which application is incorporated herein by reference in its entirety.

FIELD OF THE INVENTION

The claimed invention relates generally to the fields of medicine and enzyme bio-chemistry. More particularly, the invention relates to compounds and methods for modulating the activity of Rho C.

BACKGROUND OF THE INVENTION

The small GTPase family of proteins are central regulators of cell physiology. Five homologous subfamilies are found in the genomes of all eukaryotes; the S. cerevisiae genome includes 29 proteins in all five families, and the human genome encodes approximately 100 proteins. These five subfamilies have five overlapping but partially distinct functional roles. Ras family members regulate cell growth and division (A. Hall, Curr Opin Cell Biol (1993) 5(2): 265–68; A. B. Vojtek et al., J Biol Chem (1998) 273(32): 19925–28). Rho family members regulate cell motility, and shape through the actin skeleton (A. Hall, Science (1998) 279:509–14; D. J. Mackay et al., J Biol Chem (1998) 273:20685–88). ARF family members regulate cell adhesion and vesicle trafficking to and from the plasma membrane (A. L. Boman et al., Trends Biochem Sci (1995) 20(4):147–50; P. Chavrier et al., Curr Opin Cell Biol (1999)11(4):466–75). Rab family members regulate intra-vesicular organelle trafficking (O. Martinez et al., Biochim Biophys Acta (1998) 1404(1–2):101–12; P. Chavrier et al., supra; F. Schimmoller et al., J Biol Chem (1998) 273(35):22161–14) and Ran family members regulate nuclear translocation and chromosomal segregation through regulation of microtubule assembly at the spindle pole (M. S. Moore, J Biol Chem (1998) 273(36):22857–60; M. G. Rush et al., Bioessays (1996) 18(2):103–12). These proteins stimulate other proteins in their GTP-bound state via physical interactions, and lose these associations and activities in the post-hydrolytic GDP-bound state. The hydrolysis reaction thus serves as molecular timer for the events triggered by the GTP-bound small G-protein. In addition, these GTPases also serve as signal integrators since the GTPases are regulated by other signaling pathway proteins; these signaling proteins are themselves regulated and promote or inhibit exchange of GDP for GTP or accelerate the GTP hydrolysis reaction. Ras was the first human small-GTPase to be appreciated in detail due to its identification as a human oncogene mutated in greater than 20% of human cancers (J. L. Bos, Cancer Res (1989) 49(17):4682–89). The ras mutants found in human cancers create a GTPase deficient form of ras which thus exists predominantly in the GTP bound-activated state.

The Rho family of small GTPase comprises more than 10 members in humans and 6 members in yeast. In both organisms, control of the actin skeleton organization and localization is a major Rho function. The human Rho family is composed of three sub-families: Rho, Rac and CDC42 (K. Kaibuchi et al., Ann. Rev. Biochem. (1999) 68:459–86). These sub-families are all involved in control of the actin skeleton and cell adhesion. RhoA is the best-studied of RhoA-G group (collectively Rho) and has been closely associated with actin stress fiber formation in fibroblasts, and through its interaction with ROCK (Rho activated kinase) actin-myosin contraction leading to smooth muscle contraction. Yeast Rho1 is most homologous to human RhoA, and is found at the main site of organized actin in yeast (the bud), where it appears to regulate actin organization associated with budding. In addition, Rho1p controls cell wall biosynthetic enzyme activity of 1,3-beta-D-glucan synthase (FKS1) during its physical association with the GTP-bound Rho1p. CDC42 and Rac-1 have also been well studied. CDC42 is closely associated with filopodia or microspike formation in fibroblasts and integrin activation. Rac-1 is a downstream component of the Ras signaling pathway from growth factor receptors and is closely associated with actin rearrangements leading to lamellipodia formation in fibroblasts (A. Hall, Science (1998) 279:509–14).

Rho proteins interact with several upstream and downstream components in signaling pathways that originate at the cell membrane with either G-protein coupled receptors, CDC42 and RhoA, or growth factor receptors, such as Rac-1.

The upstream pathways from membrane receptors to the Rho protein involves PI3-Kinase, PIP3, and a Db1-homology protein that is a PIP3 receptor and catalyzes guanine nucleotide exchange of Rho; it is thus termed a GEF ("guanine nucleotide exchange factor"). The GEFs for RhoA, and its close homologue RhoC, include Db1, Net1, Ost and Vav. These proteins all have Db1 homology domains (also known as RhoGEF domains) and pleckstrin homology domains, and all activate guanine nucleotide exchange by interaction with Rho proteins through their Db1-homology domain (R. A. Cerione et al., Curr Opin Cell Biol (1996)8 (2):216–22; I. P. Whitehead et al., Biochim Biophys Acta (1997) 1332(1):F1–23). The yeast upstream pathways from the cell membrane to Rho and beyond are highly related to those found in mammalian cells and include Tor2 (yeast PI3-kinase), and Rom1/Rom2 yeast Db1-homology and pleckstrin containing GEFs (K. Tanaka et al., Curr Opin Cell Biol (1998) 10(1): 112–16). In both yeast and humans, Rho proteins are prenylated and associate, in their GDP bound states, with a guanine nucleotide-dissociation inhibitor ("GDI"). The GDI, known as RhoGDI in humans, and Rdi1p in yeast, solublizes the Rho protein and prevents its membrane association until activation by a GEF exchanges its GDP for GTP and allows its association with the membrane (T. K. Nomanbhoy et al., Biochemistry (1999) 38(6):1744–50; P. W. Read et al., Protein Sci (2000) 9(2): 376–86).

The downstream pathways from Rho family members include many functionally and structurally homologous proteins. RhoA interacts with formin family members Dia1/Dia2, and yeast Rho1p interacts with Bni1 (another formin family member), while CDC42 interacts with WASP and WASP-N, a pair of proteins organized and regulated similarly to formin members. The formin family members have binding sites for the GTP-bound forms of Rho and also actin-nucleating domains whose exposure is controlled by binding of the GTP-Rho (N. Watanabe et al., Nat Cell Biol (1999) 1(3):136–43). In addition to formin interactions, Rho proteins interact with serine/threonine kinases. RhoA interacts with ROCK kinase, which then phosphorylates proteins that control actin polymerization; it also phosphorylates myosin regulators which control contraction in smooth muscles. Yeast Rho1p interacts with PKC1 which launches a MAP kinase cascade leading to control of transcription and the actin skeleton (S. B. Helliwell et al., *Curr Biol* (1998) 8(22):1211–14; K. Tanaka et al., *Curr Opin Cell Biol* (1998)10(1):112–16).

The 3-dimensional structure of RhoA in its GTP, GDP and $Mg^{2+}$ depleted states are known (K. Ihara et al., *J Biol Chem* (1998) 273(16):9656–66; R. Maesaki et al., *Mol Cell* (1999) 4(5):793–803; T. Shimizu et al., *J Biol Chem* (2000) 275 (24):18311–17) as is the structure of RhoA-GTP in complex with an interaction domain of the downstream effector PKN (R. Maesaki et al., supra; R. Maesaki et al., *J Struct Biol* (1999) 126:166–70), and the structure of the complex of RhoA-GDP with Rho-GDI (K. Longenecker et al., *Acta Crystallogr D Biol Crystallogr* (1999) 55(Pt 9):1503–15). The structure of RhoA in complex with rhoGAP is also known (K. Rittinger et al., *Nature* (1997) 388:693–97). The structure of these molecules combined with similarly detailed data regarding Ras and the Rho family member CDC42 yield consensus molecular mechanism for the GTPase function, GEF's promotion of GDP exchange, GAP's acceleration of GTPase activity and effector stimulation by RhoA-GTP. These studies show the guanine nucleo-tide bound in a pocket surrounded by three protein loops, known as switch region-I, switch region-II and the P-loop (the phosphate-binding loop). Switch region-I and -II interact extensively with GDI, GEF and effector domains in regions that occlude each other's binding site. Switch region I and II are dramatically rearranged by GTP binding as compared to GDP-bound RhoA and this change exposes large new hydrophobic patches on the switch region surfaces. These newly exposed regions bind effectors.

The importance of Rho proteins in immune cell physiology is highlighted by the evolution of several different mechanisms to inactivate Rho-family proteins by pathogenic Clostridia species and other bacterial pathogens. These toxins are proteins that catalyze several different types of covalent modifications of the switch region-I of Rho proteins. This covalent modifications prevents the correct function of the Rho proteins (K. Aktories, *Trends Microbiol* (1997) 5(7):282–88; G. Schmidt et al., *Naturwissenschaften* (1998) 85(6):253–61). These toxins prevent leukocyte adhesion and diapeadisis and also reduce the production of some anti-bacterial metab-olites; thus these toxins confer virulence to the strains possessing them.

Recent reports have shown an important role for Rho in cancer and metastasis. In colon, breast, and lung cancer, RhoA protein expression is elevated compared to the surrounding normal tissue. In breast cancer, RhoA, Rac and CDC42 are elevated. However, RhoA is the most dramatically elevated, and RhoA levels are correlated with disease severity (G. Fritz et al., *Int J Cancer* (1999) 81(5):682–87). In pancreatic cancers, RhoC mRNA levels are elevated in com-parison to non-cancerous tissue, and the degree of RhoC elevation is positively correlated with clinical severity and negatively with patient survival. The RhoC elevated phenotype is closely associated with metastasis (H. Suwa et al., *Br J Cancer* (1998) 77(1):147–52). Furthermore, in mice, RhoA transformed-human tumor cells are more invasive than non-transformed cells (K. Yoshioka et al., *Cancer Res* (1999) 59(8):2004–10). Using in-vivo selection for mutations that cause increased metastatic potential in human melanoma cells injected into nude mice, it was recently shown that RhoC overexpression correlates with increased metastatic potential. Overexpression of RhoC from a retroviral vector by itself was sufficient to increase this potential (E. A. Clark et al., *Nature* (2000) 406:532–35). Thus, human cancers express elevated levels of Rho proteins and the degree of elevation correlates with disease severity and poor clinical prognosis.

The compelling case for the involvement of small G-protein in diseases has prompted a number of drug development attempts. Several different geranyl and farnesyl transferase inhibitors have been developed and several are now advanced in the clinic (N. E. Kohl, *Ann NY Acad Sci* (1999) 886:91–102). These inhibitors prevent farnesylation and/or geranylation of many proteins, including the small GTPases, and thus prevent their activity. These inhibitors have shown oral activity in animal models of Ras transformed tumorogenesis. Given their low selectivity and pan-prenylated protein specificity, the low toxicity and apparent high therapeutic ratio these compound have shown is surprising (D. W. End, *Invest New Drugs* (1999) 17(3):241–58; C. C. Kumar et al., *Ann NY Acad Sci* (1999) 886:122–31). An interesting approach to finding wild-type Ras inhibitors used electrospray mass spectrometry to detect compounds that form non-covalent complexes with Ras-GDP. A large library of compounds was screened and several hydroxylamine containing compounds that form complexes with the $Mg^{2+}$ and the exterior lip of switch region-II were found; this binding site was mapped using NMR and a mass-spectrometric footprinting technique. The more avid of these compounds bind with affinities of 0.9 µM (A. K. Ganguly et al., *Bioorg Med Chem* (1997) 5(5):817–20; A. K. Ganguly et al., *Biochemistry* (1998) 37(45):15631–37; A. G. Taveras et al., *Bioorg Med Chem* (1997) 5(1):125–33).

The GTPases present special problems as drug development targets. The difficulties arise due to the functions and properties of these proteins: they exist in numerous, but sometimes transient, complexes with partners (7–10 known partners for each protein). They exist inside most cells as GDP-bound enzymes in a complex with a GDI; their exchange to a GTP bound form happens instantaneously due to the high intracellular concentration of GTP (~1 mM) and their very high affinity for GTP. Their enzymatic activity and turnover is quite slow, and in a practical sense may happen only when a GAP associates with the protein. A specific issue related to discovery of mutant Ras inhibitors is that mutant-Ras forms found in tumors are GTPase deficient, and thus are GTP-bound. The Rho proteins are not locked into a single GTP-bound state, and therefore cycle between states. Thus Rho proteins may be easier targets to inhibit than mutant Ras has proven to be. However, these properties make it particularly difficult to assay small G-proteins completely in in-vitro biochemical assays.

SUMMARY OF THE INVENTION

One aspect of the invention is a compound of formula 1

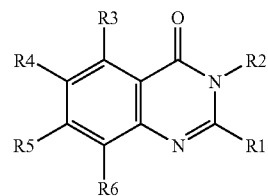

wherein $R_1$ is H, lower alkyl, aralkyl, aryl-lower alkenyl, or $-(CH_2)_n CH(R_7)NR_8R_8$, where n is 0–6 inclusive, $R_7$ is H, lower alkyl, aryl, or aralkyl, $R_8$ is H, lower alkyl, cycloalkyl, aryl, or aralkyl, and $R_9$ is R, RCO—, ROCO—, or RNHCO—, where R is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_2$ is lower alkyl, aryl, aralkyl, or —(CHR$_{10}$)$_m$—(CO)—R$_{11}$, wherein m is 0–4, $R_{10}$ is H or lower alkyl, and $R_{11}$ is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_3$, $R_4$, $R_5$, and $R_6$, are each independently H, lower alkyl, halo, nitro, OH, lower alkoxy, $NH_2$, lower alkylamino, di(lower alkylamino), trifluoromethyl, or SH; or a pharmaceutically acceptable salt thereof.

Another aspect of the invention is a method for inhibiting Rho C enzyme activity, by contacting said enzyme with a compound of formula 1.

Another aspect of the invention is a formulation for treating a disorder mediated by RhoC, comprising an effective amount of a compound of formula 1, and a pharmaceutically acceptable carrier.

DETAILED DESCRIPTION

Definitions:
Compounds of the invention are compounds of formula 1:

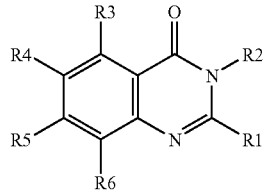

wherein $R_1$ is H, lower alkyl, aralkyl, aryl-lower alkenyl, or —(CH$_2$)$_n$CH(R$_7$)NR$_8$R$_9$, where n is 0–6 inclusive, $R_7$ is H, lower alkyl, aryl, or aralkyl, $R_8$ is H, lower alkyl, cycloalkyl, aryl, or aralkyl, and $R_9$ is R, RCO—, ROCO—, or RNHCO—, where R is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_2$ is lower alkyl, aryl, aralkyl, or —(CHR$_{10}$)$_m$—(CO)—R$_{11}$, wherein m is 0–4, $R_{10}$ is H or lower alkyl, and $R_{11}$ is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_3$, $R_4$, $R_5$, and $R_6$, are each independently H, lower alkyl, halo, nitro, OH, lower alkoxy, $NH_2$, lower alkylamino, di(lower alkylamino), trifluoromethyl, or SH; or a pharmaceutically acceptable salt thereof.

Compounds of the invention are named as quinazolin-4-ones, and are numbered as follows:

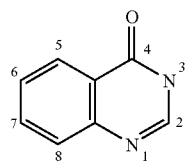

The term "alkyl" as used herein refers to a fully saturated radical consisting only of carbon and hydrogen, having from 1 to about 25 carbon atoms. The term "lower alkyl" refers to an alkyl radical having from 1 to about 6 carbon atoms, such as, for example, methyl, ethyl, propyl, isopropyl, butyl, 3-methylpentyl, hexyl, and the like.

The term "lower alkoxy" refers to a radical of the form RO—, where R is lower alkyl. Suitable examples of lower alkoxy include, without limitation, methoxy, ethoxy, propyloxy, 2-propyloxy, butoxy, t-butoxy, hexyloxy, and the like. Similarly, "lower alkylthio" refers to a radical of the form RS—, where R is lower alkyl. "Lower alkylenedioxy" refers to a diradical of the form —O—R'—O—, where R' is a lower alkyl diradical. Exemplary alkylenedioxy moieties include, without limitation, methylenedioxy, 1,2-ethylenedioxy, 2,2-propyl-enedioxy, and the like.

The term "aryl" refers to phenyl or naphthyl. "Aralkyl" refers to a moiety of the form Ar—R'—, where Ar is aryl and R' is lower alkylene. Exemplary aralkyl radicals include, without limitation, benzyl, phenethyl, 4-phenylhexyl, 2-naphthylmethyl, 1-naphthylethyl, and the like.

A "heterocyclic ring" as used herein refers to a closed loop of 3–7 atoms containing car-bon and at least one atom of O, N, S, and/or P. Heterocyclic rings can be saturated or unsaturated. Exemplary heterocyclic rings include, without limitation, piperidine, furan, tetrahydrofuran, pyrrole, triazole, pyran, tetrahydropyran, thiazole, dioxin, 2,2-dimethyl-1,3-dioxolane, and the like. Heterocyclic rings in the context of this invention will be fused to the phenyl ring that carries $R_2$, $R_3$, $R_4$, $R_5$, and $R_6$, thus forming ring systems such as, for example, benzimidazole, benzofuran, and the like.

The term "halo" as used herein refers to fluoro, chloro, bromo, and iodo.

The term "pharmaceutically acceptable" refers to compounds and derivatives that are not unacceptably toxic to an organism or tissue to be treated.

The term "salt" refers to a derivative of a compound of the invention derived by addition of a simple acid to a basic compound of the invention, or addition of a base to an acidic compound of the invention. For example, compounds of the invention can form acid addition salts, such as hydrochlorides, hydrobromides, acetates, tartarates, citrates, malonates, phosphates, nitrates, sulfates, mesylates, and the like. The term "esters" refers to derivatives of a compound of the invention derived by condensing a compound of the invention having a free —OH group with a carboxylic acid. Exemplary esters include acetates, propionates, citrates, and the like. The term "amides" refers to derivatives of a compound of the invention derived by condensing a compound of the invention having a free —NH group with a carboxylic acid. Exemplary acids include acetic, propionic, citric, malonic, and the like.

The term "modulate" refers to a detectable alteration in an observable enzymatic activity of the target enzyme. The alteration is preferably an inhibition of at least 20%.

The term "effective amount" refers to the quantity of a compound of the invention necessary to inhibit RhoC protein activity, in vitro or in vivo. Such inhibition can be accomplished directly (i.e., by binding directly to RhoC in a way that modulates one or more biological activities) or indirectly (for example, by modifying or interfering with a RhoC ligand that in turn modulates RhoC activity). A "therapeutically effective amount" refers to a quantity of a com-pound of the invention sufficient to treat a disorder mediated by RhoC activity. Treatment includes preventing or alleviating one or more symptoms of the disorder, preventing the worsening of one or more symptoms, and reducing the likelihood or probability of disease occurring or advancing. Thus, for example, administration of a compound of the invention in order to treat cancer (known or suspected), or to inhibit metastasis of known or suspected tumors, constitutes a treatment within the scope of the invention.

The term "disorder mediated by RhoC" refers to a disease state that is ameliorated by the inhibition of RhoC. Exemplary disorders include, without limitation, cancer and metastasis.

General Method:

One aspect of the invention is a compound of formula 1:

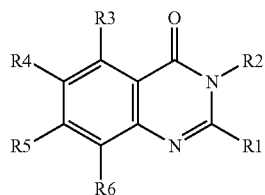

wherein $R_1$ is H, lower alkyl, aralkyl, aryl-lower alkenyl, or —$(CH_2)_n CH(R_7)NR_8 R_9$, where n is 0–6 inclusive, $R_7$ is H, lower alkyl, aryl, or aralkyl, $R_8$ is H, lower alkyl, cycloalkyl, aryl, or aralkyl, and $R_9$ is R, RCO—, ROCO—, or RNHCO—, where R is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_2$ is lower alkyl, aryl, aralkyl, or —$(CHR_{10})_m$—(CO)—$R_{11}$, wherein m is 0–4, $R_{10}$ is H or lower alkyl, and $R_{11}$ is lower alkyl, cycloalkyl, aryl, or aralkyl, wherein aryl and aralkyl are substituted with 0–3 substituents selected from the group consisting of lower alkyl, halo, nitro, —OH, trifluoromethyl, or lower alkoxy; $R_3$, $R_4$, $R_5$, and $R_6$, are each independently H, lower alkyl, halo, nitro, OH, lower alkoxy, $NH_2$, lower alkylamino, di(lower alkylamino), trifluoromethyl, or SH; or a pharmaceutically acceptable salt thereof.

Compounds of the invention are synthesized according to general procedures known in the chemical arts, such as, for example: "Synthesis of the quinazolinone ring from anthranilic acid", J. Fetter, et al., *Tetrahedron* (1991) 47(45): 9393–410; "Reaction with arylamines", M. A. Sayed et al., *Indian J. Chem.* (1991)30(B):980–83; "Bromination with bromine in AcOH/AcONa" I. Hermecz et al., *Heterocycles* (1994) 34(2):903–14, all incorporated herein by reference in full.

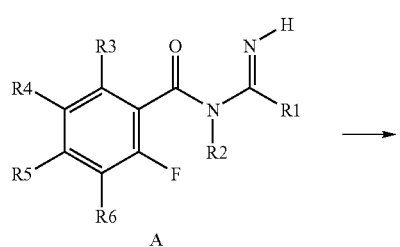

A

Multiple synthetic schemes can be employed to obtain the compounds of this invention. The sequence selected is dependent on the availability of reagents and pivotal intermediates, and reaction and protecting group compatibilities.

Cyclization of the intermediate ortho-[fluoro (or halo) benzoyl]amidine A, in the presence of a suitable base (for example, trialkylamine, potassium carbonate, or suitable equivalent reagent) and an inert solvent (for example, a lower alkanol, dimethylformamide, N-methylpyrrolidone, dimethylsulfoxide or suitable equivalent solvent) affords the quinazolinones C. Alternatively, cyclization of the ortho (acylamido)benzamides B, in the presence of a dehydrating agent (for example, sulfuric acid, phosphoric acid, dicyclohexylcarbodiimide, methanesulfonyl halide-trialkylamine, phosphorus oxychloride or suitable equivalent reagents) affords compound C.

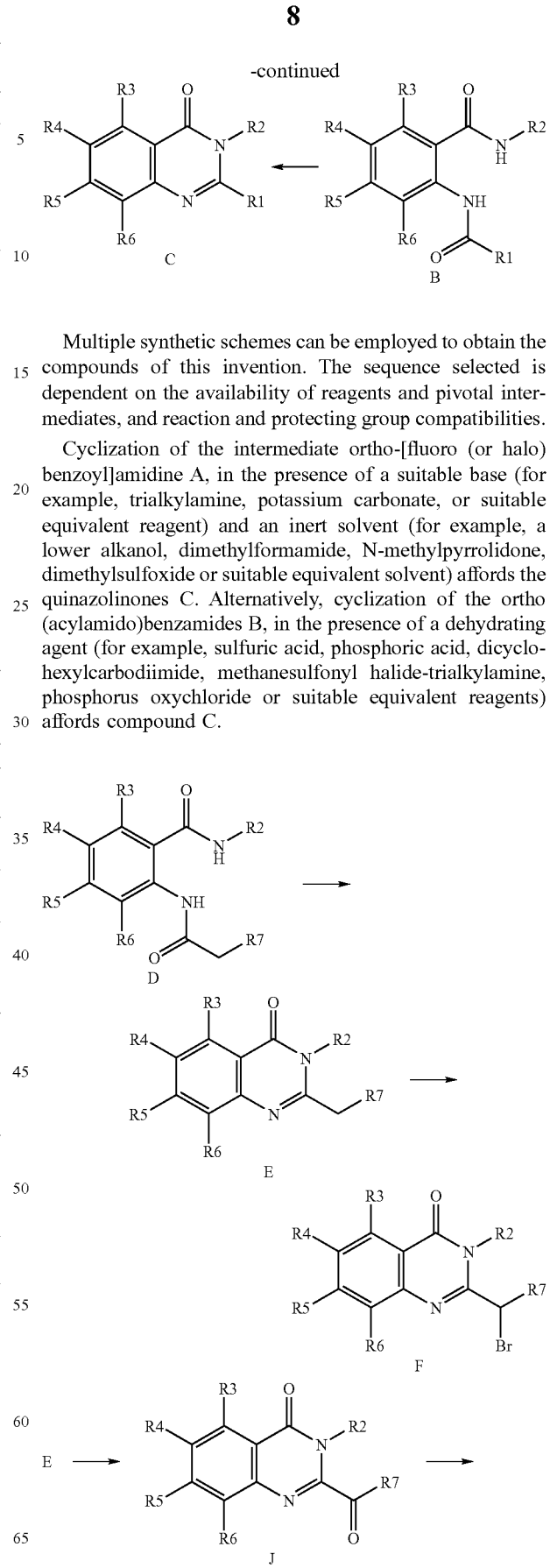

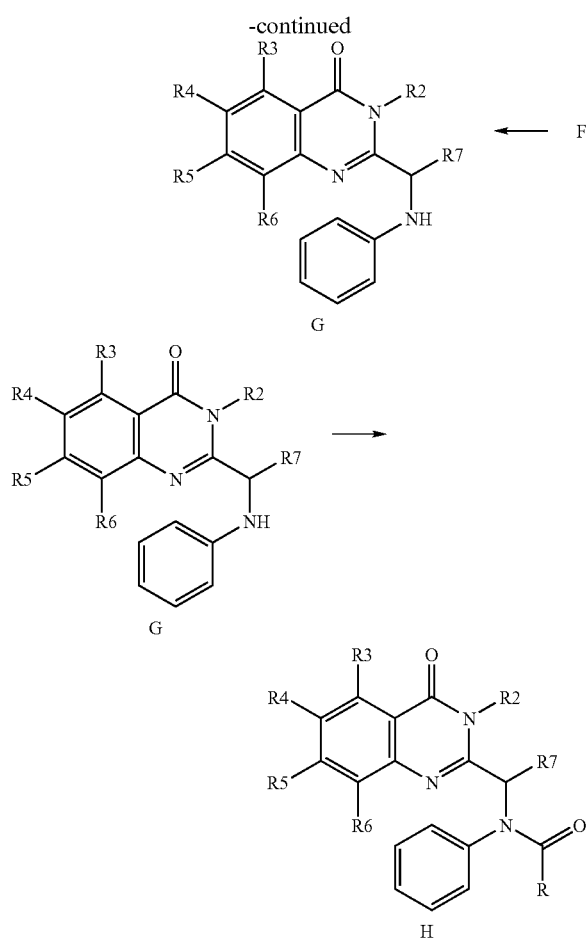

More functionalized quinazolinone final products G and H are obtained from other reaction sequences (E→F→G→H or E→J→G→H). Bromination of intermediate E is performed with bromine in excess acetic acid at a temperature of about 25 to about 100° C. The bromoquinazolinone F, on treatment with appropriate substituted aniline in an inert solvent (for example, trialkylamine, dimethyl-formamide, N-methylpyrrolidone, and the like), affords the anilinoquinazolinone G. Intermediate G, on treatment with an appropriate acylating agent (for example, lower alkylisocyanates, acyl halides, acyl anhydrides, aroyl halides, aroyl anhydrides, or thiol esters), affords H.

A different procedure (E→J→G→H) is employable when pivotal intermediates are difficult to obtain. Specifically, intermediate E is oxidized to the ketoquinazolinone J in the presence of either a heterogeneous oxidant (e.g., activated manganese dioxide, nickel peroxide, or appropriate equivalent reagent) or a homogeneous oxidant (e.g., tetracyanobenzoquinone, dichlorodicyanobenzoquinone, Salcomine). Treatment of the ketone J with an appropriate aniline affords an intermediate arylimine which is reduced in situ (for example, using sodium cyanoborohydride, sodium tris(acetoxy)borohydride, diborane, borane-methyl sulfide, aluminum hydride, or equivalent reducing agents) to afford G.

Compounds of the invention are assayed for activity using any convenient biochemical or biological assay. For example, one can examine compounds for binding to recombinantly-expressed RhoC, assay compounds for their ability to reverse a RhoC-induced phenotype in a heterologous cell (see e.g., WO99/24563, incorporated herein by reference), or using one or more of the experimental protocols described in the references cited herein. Compounds of the invention demonstrated activity in surrogate genetic assays, in which mammalian RhoA and RhoC proteins were expressed in yeast, producing a screenable phenotype. An effective concentration of test compound specifically reversed the phenotype, demonstrating activity. Com-pounds were also examined for inhibition of stress fibers, by stimulating NIH 3T3 cells with 10 µM LPA in DMEM+0.2% FBS in the presence of test compounds for 4 hours. Staining with Rhodamine-phalloidin post fixation demonstrated a dose-dependent reduction in the percentage of labeled F-actin, demonstrating inhibition of a RhoC biological activity.

Compounds of the invention can be administered to a subject, or can be applied directly to cells, for example in a cell culture. If administered to a cell culture, the compound is preferably first suspended or dissolved in a suitable carrier. Suitable carriers include, without limitation, water, saline solution, dimethylsulfoxide (DMSO) and solutions thereof, cell culture media, and the like.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

A compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. One can administer compounds of the invention by direct injection into a tumor. The formulation can be administered in a single unit dosage form for continuous treatment or in a single unit dosage form ad libitum when relief of symptoms is specifically required.

The effective dose of a compound of the invention will depend on the condition to be treated, the potency and absorption rate of the compound as formulated, the mode of administration, the age, weight, and health of the subject, and the like, and thus cannot be specified in advance. However, it is possible to estimate the dosage by methods known in the art. For example, one can obtain tumor cells from a patient by biopsy, and directly determine the concentration of a compound of the invention that is effective to inhibit the growth of cancerous tissue. From this measurement, one can calculate a dosage (depending on the route of administration) suitable for the patient.

EXAMPLE

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at ambient temperature and pressure.

Example 1

Compound Preparation (A) A mixture of N-(1-benzoylethyl)-2-(formylamino)-benzamide in N-methyl-pyrrolidone ("NMP") is dehydrated with concentrated sulfuric acid, cyclizing to provide 3-(1-phenyl-1-oxoprop-2-yl)-quinazolin-4-one.

(B) Similarly, proceeding as in part (A) above, but substituting N-(1-benzoyl-ethyl)-2-(formylamino)-5-bromo-benzamide, N-phenyl-2-cinnamoylamino-benzamide, N-phenyl-2-(4-nitro)cinnamoylamino-benzamide, N-(2,4-dichlorophenyl)-2-(4-nitro)cinnamoylamino-benzamide, N-phenyl-2-(3-bromo-4-methoxy)cinnamoylamino-benzamide, and N-(2,4-dichlorophenyl)-2-(3-bromo-4-methoxy) cinnamoylamino-benzamide for N-(1-benzoylethyl)-2-(formylamino)-benzamide, the following compounds are prepared:

3-(1-phenyl-1-oxoprop-2-yl)-6-bromo-quinazolin-4-one;
2-styryl-3-phenyl-quinazolin-4-one;
2-(4-nitrostyryl)-3-phenyl-quinazolin-4-one;
2-(4-nitrostyryl)-3-(2,4-dichlorophenyl)-quinazolin-4-one;
2-(3-bromo-4-methoxystyryl)-3-phenyl-quinazolin-4-one; and
2-(3-bromo-4-methoxystyryl)-3-(2,4-dichlorophenyl)-quinazolin-4-one.

(C) 2-Ethyl-3-benzyl-quinazolin-4-one is prepared following the procedure set forth in part (A) above, but substituting N-benzyl-2-(propanoylamino)-benzamide for N-(1-benzoylethyl)-2-(formylamino)-benzamide ("Compound E"). Compound E is brominated by heating in acetic acid with bromine to provide 2-(1-bromoethyl)-3-benzyl-quinazolin-4-one ("Compound F"). Compound F is treated with 4-methoxy-aniline in triethylamine to provide 2-(1-(4-methoxyphenylamino)ethyl)-3-benzyl-quinazolin-4-one ("Compound G"). Compound G is then acylated with benzoyl chloride to provide 2-(1-(N-benzoyl-N-(4-methoxyphenyl)-aminoethyl)-3-benzyl-quinazolin-4-one.

(D) Proceeding as in part (C) above, but substituting 3-chloroaniline, 3,4-di-methylaniline, and 4-trifluoromethylaniline for 4-methoxyaniline, the following compounds are prepared:

2-(1-(N-benzoyl-N-(3-chlorophenyl)-aminoethyl)-3-benzyl-quinazolin-4-one;
2-(-1-(N-benzoyl-N-(3,4-dimethylphenyl)-aminoethyl)-3-benzyl-quinazolin-4-one; and
2-(1-(N-benzoyl-N-(4-trifluoromethylphenyl)-aminoethyl)-3-benzyl-quinazolin-4-one.

(E) Proceeding as in parts (C) and (D) above, but substituting butanoyl chloride, 3,4-dimethoxybenzoyl chloride, and cyclohexyl isocyanate for benzoyl chloride, the following compounds are prepared:

2-(1-(N-butanoyl-N-(4-methoxyphenyl)-aminoethyl)-3-benzyl-quinazolin-4-one;
2-(1-(N-(3,4-dimethoxybenzoyl)-N-(4-methoxyphenyl)-aminoethyl)-3-benzyl-quinazolin-4-one;
2-(1-(N-(cyclohexyl-ureido)-N-(4-methoxyphenyl)-aminoethyl)-3-benzyl-quinazolin-4-one;
2-(1-(N-butanoyl-N-(3-chlorophenyl)-aminoethyl)-3-benzyl-quinazolin-4-one;
2-(1-(N-(3,4-dimethoxybenzoyl)-N-(3,4-dimethylphenyl)-aminoethyl)-3-benzyl-quinazolin-4-one;
2-(1-(cyclohexyl-ureido)-N-(4-trifluoromethylphenyl)-aminoethyl)-3-benzyl-quinazolin-4-one;
2-(1-(N-butanoyl-N-(3-chlorophenyl)-aminoethyl)-3-benzyl-quinazolin-4-one;
2-(1-(N-(3,4-dimethoxybenzoyl)-N-(3,4-dimethylphenyl)-aminoethyl)-3-benzyl-quinazolin-4-one; and
2-(1-(N-(cyclohexyl-ureido)-N-(4-trifluoromethylphenyl)-aminoethyl)-3-benzyl-quinazolin-4-one.

(F) Proceeding as in parts (C)-(E) above, but substituting N-phenethyl-2-(propanoylamino)-benzamide, N-(4-chlorobenzyl)-2-(propanoylamino)-benzamide, and N-benzyl-2-(3-methylbutanoylamino)-benzamide for N-benzyl-2-(propanoylamino)-benzamide, the following compounds are prepared:

2-(1-(N-benzoyl-N-(4-methoxyphenyl)-aminoethyl)-3-phenethyl-quinazolin-4-one;
2-(1-(N-benzoyl-N-(3-chlorophenyl)-aminoethyl)-3-phenethyl-quinazolin-4-one;
2-(1-(N-benzoyl-N-(3,4-dimethylphenyl)-aminoethyl)-3-phenethyl-quinazolin-4-one;
2-(1-(N-benzoyl-N-(4-trifluoromethylphenyl)-aminoethyl)-3-phenethyl-quinazolin-4-one;
2-(1-(N-butanoyl-N-(4-methoxyphenyl)-aminoethyl)-3-phenethyl-quinazolin-4-one;
2-(1-(N-(3,4-dimethoxybenzoyl)-N-(4-methoxyphenyl)-aminoethyl)-3-phenethyl-quinazolin-4-one;
2-(1-(N-(cyclohexyl-ureido)-N-(4-methoxyphenyl)-aminoethyl)-3-phenethyl-quinazolin-4-one;
2-(1-(N-butanoyl-N-(3-chlorophenyl)-aminoethyl)-3-phenethyl-quinazolin-4-one;
2-(1-(N-(3,4-dimethoxybenzoyl)-N-(3,4-dimethylphenyl)-aminoethyl)-3-phenethyl-quinazolin-4-one;
2-(1-(N-(cyclohexyl-ureido)-N-(4-trifluoromethylphenyl)-aminoethyl)-3-phenethyl-quinazolin-4-one;
2-(1-(N-butanoyl-N-(3-chlorophenyl)-aminoethyl)-3-phenethyl-quinazolin-4-one;
2-(1-(N-(3,4-dimethoxybenzoyl)-N-(3,4-dimethylphenyl)-aminoethyl)-3-phenethyl-quinazolin-4-one;
2-(1-(N-(cyclohexyl-ureido)-N-(4-trifluoromethylphenyl)-aminoethyl)-3-phenethyl-quinazolin-4-one;
2-(1-(N-benzoyl-N-(4-methoxyphenyl)-aminoethyl)-3-phenethyl-quinazolin-4-one;
2-(1-(N-benzoyl-N-(3-chlorophenyl)-aminoethyl)-3-(4-chlorobenzyl)-quinazolin-4-one;
2-(1-(N-benzoyl-N-(3,4-dimethylphenyl)-aminoethyl)-3-(4-chlorobenzyl)-quinazolin-4-one;
2-(1-(N-benzoyl-N-(4-trifluoromethylphenyl)-aminoethyl)-3-(4-chlorobenzyl)-quinazolin-4-one;
2-(1-(N-butanoyl-N-(4-methoxyphenyl)-aminoethyl)-3-(4-chlorobenzyl)-quinazolin-4-one;
2-(1-(N-(3,4-dimethoxybenzoyl)-N-(4-methoxyphenyl)-aminoethyl)-3-(4-chlorobenzyl)-quinazolin-4-one;
2-(1-(N-(cyclohexyl-ureido)-N-(4-methoxyphenyl)-aminoethyl)-3-(4-chlorobenzyl)-quinazolin-4-one;
2-(1-(N-butanoyl-N-(3-chlorophenyl)-aminoethyl)-3-(4-chlorobenzyl)-quinazolin-4-one;
2-(1-(N-(3,4-dimethoxybenzoyl)-N-(3,4-dimethylphenyl)-aminoethyl)-3-(4-chlorobenzyl)-quinazolin-4-one;
2-(1-(N-(cyclohexyl-ureido)-N-(4-trifluoromethylphenyl)-aminoethyl)-3-(4-chlorobenzyl)-quinazolin-4-one;

2-(1-(N-butanoyl-N-(3-chlorophenyl)-aminoethyl)-3-(4-chlorobenzyl)-quinazolin-4-one;

2-(1-(N-(3,4-dimethoxybenzoyl)-N-(3,4-dimethylphenyl)-aminoethyl)-3-(4-chlorobenzyl)-quinazolin-4-one;

2-(1-(N-(cyclohexyl-ureido)-N-(4-trifluoromethylphenyl)-aminoethyl)-3-(4-chlorobenzyl)-quinazolin-4-one;

2-(1-(N-benzoyl-N-(4-methoxyphenyl)-aminoethyl)-3-phenethyl-quinazolin-4-one;

2-(1-(N-benzoyl-N-(3-chlorophenyl)-aminoethyl)-3-benzyl-quinazolin-4-one;

2-(1-(N-benzoyl-N-(3,4-dimethylphenyl)-amino-3-methylbutyl)-3-benzyl-quinazolin-4-one;

2-(1-(N-benzoyl-N-(4-trifluoromethylphenyl)-amino-3-methylbutyl)-3-benzyl-quinazolin-4-one;

2-(1-(N-butanoyl-N-(4-methoxyphenyl)-amino-3-methylbutyl)-3-benzyl-quinazolin-4-one;

2-(1-(N-(3,4-dimethoxybenzoyl)-N-(4-methoxyphenyl)-amino-3-methylbutyl)-3-benzyl-quinazolin-4-one;

2-(1-(N-(cyclohexyl-ureido)-N-(4-methoxyphenyl)-amino-3-methylbutyl)-3-benzyl-quinazolin-4-one;

2-(1-(N-butanoyl-N-(3-chlorophenyl)-amino-3-methylbutyl)-3-benzyl-quinazolin-4-one;

2-(1-(N-(3,4-dimethoxybenzoyl)-N-(3,4-dimethylphenyl)-amino-3-methylbutyl)-3-benzyl-quinazolin-4-one;

2-(1-(N-(cyclohexyl-ureido)-N-(4-trifluoromethylphenyl)-amino-3-methylbutyl)-3-benzyl-quinazolin-4-one;

2-(1-(N-butanoyl-N-(3-chlorophenyl)-amino-3-methylbutyl)-3-benzyl-quinazolin-4-one;

2-(1-(N-(3,4-dimethoxybenzoyl)-N-(3,4-dimethylphenyl)-amino-3-methylbutyl)-3-benzyl-quinazolin-4-one; and 2-(-1(N-(cyclohexyl-ureido)-N-(4-trifluoromethylphenyl)-amino-3-methylbutyl)-3-benzyl-quinazolin-4-one.

Example 2

Formulations

The following example illustrates the preparation of representative pharmaceutical formulations containing an active compound of formula 1:

| Active compound | 0.01 g |
|---|---|
| Propylene glycol | 20.0 g |
| Polyethylene glycol 400 | 20.0 g |
| Tween ® 80 | 1.0 g |
| 0.9% Saline solution qs | 100.0 ml |

The active compound is dissolved in propylene glycol, polyethylene glycol 400 and Tween 80. A sufficient quantity of 0.9% saline solution is then added with stirring to provide 100 mL of the I.V. solution which is filtered through a 0.2 µm membrane filter and packaged under sterile conditions.

(B) Tablet Formulation:

| | parts by weight |
|---|---|
| Active compound | 25.0 |
| Magnesium stearate | 0.2 |
| Pregelatinized starch | 74.8 |

The above ingredients are dry-blended and loaded into #0 capsules containing about 100 mg active compound per capsule.

Example 3

Assay Construction (A) cDNAs corresponding to the complete open reading frame of RhoC were PCR amplified from pooled total cDNAs initially synthesized from placental, fetal brain, and fetal liver poly(A)$^+$ mRNAs (Clontech Laboratories, Inc.). First and second strand cDNA synthesis was performed using Superscript II reverse transcriptase (Life Technologies, Inc.) as previously described (E. L. Perkins et al., *Proc Natl Acad Sci USA* (1999) 96(5):2204–09). The 5' and 3' oligonucleotides for amplification were, respectively, RhoC 5' (5' CAAAAAATTGTTAATATACCTCTATACTTTAAC GTCAAGGGGATCCatggctgcaatccgaaagaag3') and RhoC 3' (5'CAGTTGAAGTGAACTTGCGGGGTTTTTCAGTA TCTACGATTCATCTGCAGtcagagaatgggacagccccct3').

PCR amplification was carried out using Bio-X-ACT (Bioline USA Inc., Kenilworth, N.J.) thermostable DNA polymerase according to the manufacturer's instructions. Oligonucleotides were designed to amplify their target cDNAs and carry approximately 45 base pairs of homology at their 5' ends with the yeast expression vector pARC25B (GenBank AF359244) or its close relative pARC35B. The pARC35B vector contains the yeast GAL1 promoter, GAL4 transcription terminator, ARS sequence for replication, CEN sequence for mitotic transmission, and the LEU2 gene for selection in yeast.

After PCR, approximately 200 ng of amplified cDNA was cotransformed with approximately 100 ng of vector into yeast and transformants were selected for leucine prototrophy. Homologous recombination of the target cDNAs into pARC35B was confirmed by yeast whole cell PCR. Plasmids from at least three independent transformants were subsequently rescued into the *E. coli* strain DH5alpha via electroporation, and further characterized by restriction enzyme analysis and DNA sequencing of the RhoC open reading frame. The insert sequence was confirmed as identical to that of GenBank BC009177 (and many other RhoC clones).

Purified and sequenced RhoC expression plasmid was then linearized with SfiI which simultaneously removes the CEN/ARS sequence, and exposes 45 nucleotide segments that match to the 5' and 3' regions of the LYS2 gene, so that integration at the LYS2 locus can be detected. The linear plasmid was transformed into the yeast strain EIS20-2B and selected for leucine prototrophy. These colonies were then replica-plated to alpha amino-adipate plates to screen for those which had become lysine auxotrophs, indicating the replacement of the LYS2 gene with the expression vector. Several individual alpha-amino adipate-resistant transformants were clonally purified by streaking to rich media, and proper integration at the LYS2 locus was confirmed by whole cell PCR.

(B) Several correctly integrated isolates and controls were grown to saturation in synthetic media with 2% glucose (repressed) in a microtiter dish overnight at 30° C. The cultures were then diluted 1:400 into synthetic media with 2% galactose to induce expression of the RhoC protein. Measurements of culture density by absorbance at 600 nm were taken at intervals for approximately 48 hours. Growth inhibition was calculated relative to cells harboring integrated empty vector. RhoC-expressing cells typically grow to an optical density of about 20% that of vector alone after about 42 hours. This is scored as 80% growth inhibition.

A yeast strain expressing RhoC as described above was then screened against a library of over 110,000 low molecular weight organic compounds which represents a diverse collection derived from multiple commercial sources. All screening was done with initial compound concentrations of 5 μg/ml. Cells were grown overnight in synthetic media with 2% glucose (repressed) to late logarithmic/early stationary phase. The next day cells were washed once with synthetic media without a carbon source and diluted to a final $OD_{600}$ of 0.02 in synthetic media containing 2% galactose (induced). The diluted cells (90 μl) were added immediately to 96-well plates containing the test compound. The final volume in each well was 100 μl, and contained DMSO at a final concentration of 1%. As a control, cells containing vector (EIS20-2B with integrated vector plasmid) were similarly grown, washed and diluted to the same OD and then inoculated.

The plates were incubated at 30° C. for 40–42 hrs, and the $OD_{600}$ was read with a microtiter plate reader (Molecular Device, Menlo Park, Calif.) after shaking. The effect of compounds was measured as percent of growth restoration using the following equation: Percent Growth Restoration= (TEST−MEDarc)/(MEDvec−MEDarc)×100, where TEST is the $OD_{600}$ of the well with test compound, MEDarc is the median value of $OD_{600}$ of the cells without compound, and MEDvec is the median value of $OD_{600}$ of vector-containing cells. Compounds showing ☐20% growth restoration were scored as hits. Compounds were later obtained in powder form and retested in dilutions from 0.5 μM to 128 μM.

(C) The compounds listed in the Table below showed excellent potency. The therapeutic index listed is derived by dividing the $EC_{50}$s by the $CC_{50}$ values.

| Structure | Compound | $EC_{50}$ | $CC_{50}$ | Index |
|---|---|---|---|---|
| 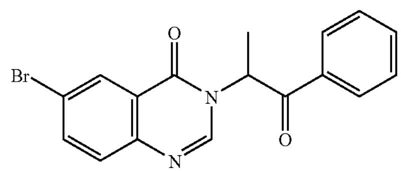 | 3-(1-phenyl-1-oxoprop-2-yl)-6-bromo-quinazolin-4-one | | | |
| 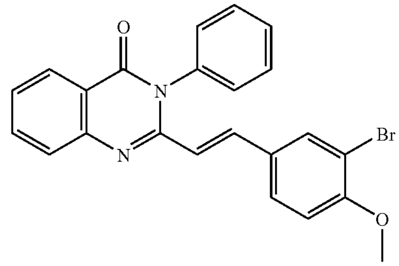 | 2-(3-bromo-4-methoxy)styryl-3-phenyl-quinazolin-4-one | | | |
|  | 2-(4-nitro)styryl-3-(2,4-dichlorophenyl)-quinazolin-4-one | | | |
| 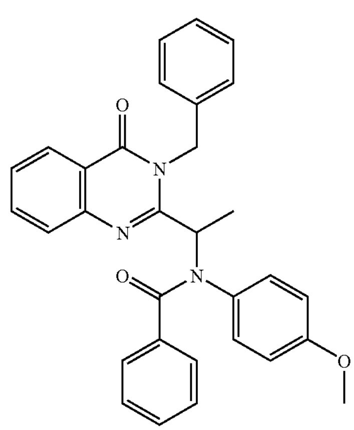 | 2-(1-(N-benzoyl-N-(4-methoxy)-phenyl)-aminoethyl)-3-benzyl-quinazolin-4-one | | | |

| Structure | Compound | EC$_{50}$ | CC$_{50}$ | Index |
|---|---|---|---|---|
| 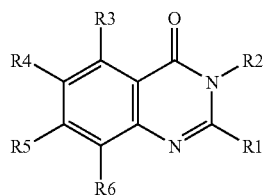 | 2-(1-(N-(3,4-dimethylphenyl)-N-(cyclohexylaminocarbonyl)-amino-ethyl)-3-benzyl-quinazolin-4-one | | | |

(D) Chemotaxis: Chemotaxis was carried out using ChemoTX plates obtained from Neuroprobe Inc. (Gaithersburg, Md.). A monocyte cell line, THP-1, was obtained from ATCC. The cells were pretreated with 30 μM compound in RPMI medium containing 10% fetal bovine serum for 2 hours, washed twice with the same medium without serum, and resuspended in the serum-free medium containing 30 μM compound. The monocyte chemoattractant protein-1 (MCP-1) was diluted in the serum free RPMI medium to 0.25 nM and aliquoted into the wells of the ChemoTX plate. The framed membrane filter (8 μm pore size) was assembled and the cells (100,000 cells in 60 μl) were loaded on top of the filter areas. The ChemoTX plate was incubated at 37° C. for 2 hours. After removing the framed filter, the plate was centrifuged and the cells in each well were labeled with 5 μM Calcein AM (Molecular Probes) for 1 hour at 37° C. The cells were washed once with PBS and fluorescence was measured at excitation wavelength of 485 nm and emission of 538 nm. The results shown are the mean absorbance readings from quadruplicate wells for each parameter

What is claimed:

1. A compound of the formula:

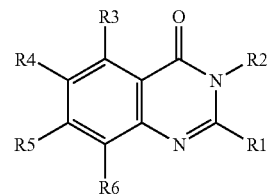

wherein $R_1$ is 3-bromo-4-methoxy-styryl and $R_2$ is phenyl;
$R_3$, $R_4$, $R_5$, and $R_6$, are each H;
or a pharmaceutically acceptable salt thereof.

2. A compound the formula:

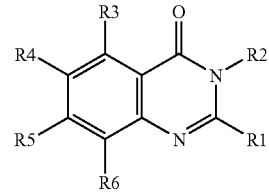

wherein $R_1$ is 4-nitro-styryl and $R_2$ is 2,4-dichlorophenyl;
$R_3$, $R_4$, $R_5$, and $R_6$, are each H;
or a pharmaceutically acceptable salt thereof.

3. A compound of the formula:

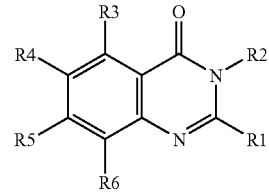

wherein $R_1$ is 1-(N-benzoyl-N-(4-methoxy-)phenyl)aminoethyl and $R_2$ is benzyl;
$R_3$, $R_4$, $R_5$, and $R_6$, are each H;
or a pharmaceutically acceptable salt thereof.

4. A compound of the formula:

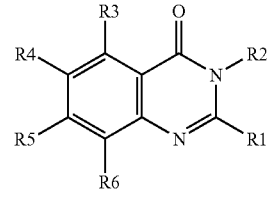

wherein $R_1$ is 1-(N-(3,4-dimethylphenyl)-N-(cyclohexyaminocarbonyl)-aminoethyl and $R_2$ is benzyl;
$R_3$, $R_4$, $R_5$, and $R_6$, are each H;
or a pharmaceutically acceptable salt thereof.

* * * * *